(12) United States Patent
Kim

(10) Patent No.: US 7,153,328 B2
(45) Date of Patent: Dec. 26, 2006

(54) ARTIFICIAL HIP JOINT PROSTHESIS

(76) Inventor: Sung-kon Kim, 201-304 Hanjin Apt. Donam 2-dong, Songbok-gu 136-753, Seoul (KR)

( * ) Notice: Subject to any disclaimer, the term of this patent is extended or adjusted under 35 U.S.C. 154(b) by 89 days.

(21) Appl. No.: 10/487,504

(22) PCT Filed: Aug. 21, 2002

(86) PCT No.: PCT/KR02/01579

§ 371 (c)(1),
(2), (4) Date: Feb. 20, 2004

(87) PCT Pub. No.: WO03/049649

PCT Pub. Date: Jun. 19, 2003

(65) Prior Publication Data

US 2004/0204767 A1 Oct. 14, 2004

(30) Foreign Application Priority Data

Aug. 21, 2001 (KR) .................. 2001-0025342 U

(51) Int. Cl.
*A61F 2/32* (2006.01)

(52) U.S. Cl. .................. 623/22.19; 623/22.28; 623/22.3

(58) Field of Classification Search ............. 623/22.17, 623/22.19, 22.2, 22.28, 22.29, 22.3
See application file for complete search history.

(56) References Cited

U.S. PATENT DOCUMENTS

| 3,863,273 | A |   | 2/1975 | Averll |
| 4,241,463 | A |   | 12/1980 | Khovaylo |
| 4,676,798 | A |   | 6/1987 | Noiles |
| 4,714,477 | A | * | 12/1987 | Fichera et al. ............ 623/22.19 |
| 4,770,659 | A | * | 9/1988 | Kendall .................... 623/22.19 |
| 5,425,779 | A | * | 6/1995 | Schlosser et al. .......... 623/22.2 |

* cited by examiner

Primary Examiner—Bruce E. Snow
(74) Attorney, Agent, or Firm—Dergosits & Noah LLP

(57) ABSTRACT

The present invention is related to an artificial hip joint prosthesis. Also, it can be decreased the time of medical treatment and administered medicine easily. Besides, it can be applied an Oriental having small pelvis.

26 Claims, 18 Drawing Sheets

ARTIFICIAL HIP JOINT PROSTHESIS

TECHNICAL FIELD

The present invention relates, in general, to an artificial hip joint prosthesis and, more particularly, to an artificial hip joint prosthesis for connecting a pelvis with a femur, which is improved in its construction.

BACKGROUND OF THE INVENTION

As well known to those skilled in the art, among a number of joints in the human body, the pelvis and the femur can be rotated relating to one another within a predetermined angle. To this end, between the pelvis and the femur, there is intervened a hip joint for connecting the pelvis and the femur with each other in a rotatable manner.

The hip joint may be adversely influenced by stand-up walking, or may be injured by inherited factors, due to excessive exercise or through an accident. In the case that the hip joint is adversely influenced or injured, pain is caused at a boundary region where the pelvis and the femur are connected with each other. In order to replace the injured hip joint and ensure smooth rotation of the hip, an artificial hip joint prosthesis is provided. The artificial hip joint prosthesis has mainly been researched at the West with the progress in medical science, and therefore, fabricated in conformity with a body structure of a Westerner who has a larger physique and bone size than an Oriental.

Hereafter, several of the conventional artificial hip joint prostheses disclosed in the art will be briefly described.

The conventional artificial hip joint prosthesis shown in FIG. 16 comprises a pelvis-contacting element 110 fastened to a pelvis, a stem 150 fastened to a femur, a head 120 integrally formed at a distal end of the stem 150, a flexible joint member 130 which is coupled to the pelvis-contacting element 110 and in which the head 120 is accommodated in a freely rotatable manner, and a release prevention member 160 for preventing release of the flexible joint member 130 from the pelvis-contacting element 110.

The release prevention member 160 is meshed with the flexible joint member 130 along a circumferential direction through engagement between prominences and depressions (see the section 'A'). An inner surface of the pelvis-contacting element 110 is defined with a groove 170, and the release prevention member 160 is formed with a projection 161 which is engaged into the groove 170.

The conventional artificial hip joint prosthesis constructed as mentioned above suffers from defects in that, since the flexible joint member 130 and the release prevention member 160 are formed as separate component parts, not only the number of component parts is increased, but also appreciable wear may take place due to rotation occurring therebetween.

Also, because the flexible joint member 130 and the release prevention member 160 are decreased in thickness at a region wherein they are meshed with each other through engagement between the prominences and the depressions, when the artificial hip joint prosthesis is used for an extended period of time, the region cannot but be weakened. Further, when the release prevention member 160 and the flexible joint member 130 are meshed with each other, since a height of a release preventing configuration of the release prevention member 160 is substantial, the stem 150 integrally rotated with the head 120 is likely to come into collision with the release prevention member 160. Therefore, if this collision occurs, as the rotation of the head 120 is interfered with, inordinate force can applied to the pelvis-contacting element 110, whereby the possibility of the pelvis to be adversely influenced is increased. Moreover, even with the flexible joint member 130 inserted into the pelvis-contacting element 110, positional fluctuation occurs due to play existing between the release prevention member 160 and the pelvis-contacting element 110 and the flexible joint member 130 and play existing between the flexible joint member 130 and the head 120, so that collision may easily occur between respective component parts.

Another conventional artificial hip joint prosthesis as shown in FIG. 17 also has the flexible joint member 130a inserted into the pelvis-contacting element 110a. The flexible joint member 130a is formed with six coupling portions 160a through 160f which are separated one from another in the circumferential direction and each of which is defined with a groove 161a.

In this type of conventional artificial hip joint prosthesis, because the six coupling portions 160a through 160f are formed separately one from another, flexibility of the flexible joint member 130a is increased. However, when it is necessary to disassemble the flexible joint member 130a from the pelvis-contacting element 110a, all of the six coupling portions 160a through 160f should be simultaneously and resiliently contracted radially inward. Hence, where it is necessary to perform an operation again for the hip joint after decoupling the flexible joint member 130a and the pelvis-contacting element 110a from each other, inconvenience is caused.

Furthermore, in order to ensure decoupling of the flexible joint member 130a from the pelvis-contacting element 110a, the groove 161a must be defined on each of the coupling portions 160a through 160f in the circumferential direction. Thus, when the head (not shown) is, inserted into a flexible joint member 130a of increased size and rotated, the stem (not shown) is apt to collide with the flexible joint member 130a.

Still another conventional artificial hip joint prosthesis as shown in FIG. 18 also has the head 120b, which is integrally formed at the distal end of the stem 150b. After the flexible joint member 130b is inserted into the pelvis-contacting element 110b, the head 120b is inserted into the flexible joint member 130b along with a support piece 162 which is placed around the head 120b. Then, a fixed locking piece 160b is fitted between the pelvis-contacting element 110b and the support piece 162 to allow the support piece 162 to be biased against the head 120b and thereby properly support the rotation of the head 120b. By the cooperation of the fixed locking piece 160b with the support piece 162, release of the head 120b and flexible joint member 130b from the pelvis-contacting element 110b is prevented.

Nevertheless, the conventional artificial hip joint prosthesis having been just described above encounters a problem in that, after the head 120b is inserted into the flexible joint member 130b, there exists a space C between the flexible joint member 130b and the fixed locking piece 160b, in which the support piece 162 can be moved, whereby collision may still occur between the head 120b and the flexible joint member 130b. Also, since the support piece 162 should be separately prepared, the entire manufacturing procedure is complicated. Further, since the increased number of component parts, that is, the flexible joint member 130b, the fixed locking piece 160b and the support piece 162 must be assembled in the pelvis-contacting element 10b, assemblability is deteriorated.

The above-described conventional artificial hip joint prostheses additionally have a disadvantage in that, since sizes of the artificial hip joint prostheses are substantial, difficulties are encountered when installing them. In other words, because the region where ends of the pelvis and femur are positioned is narrow, if assembling and disassembling operations are made complicated, difficulties cannot but be encountered when installing the artificial hip joint prostheses. In addition, because the conventional artificial hip joint prostheses are initially developed for Westerners who have large physiques and bone sizes, they cannot be appropriately adapted to Orientals.

Besides, in each of the conventional artificial hip joint prostheses, since the play in which the head can be moved to and for exists, collision frequently occurs between the head and the flexible joint member, whereby drawbacks associated with abrasion and wear of the component parts may be caused.

SUMMARY OF THE INVENTION

Accordingly, the present invention solves the above problems occurring in the prior art. An, object of the present invention is to provide an artificial hip joint prosthesis that can be more easily installed utilizing a shorter installation time.

Another object of the present invention is to provide an artificial hip joint prosthesis which can be optimally adapted even to Orientals having relatively small physiques and bone sizes.

Another object of the present invention is to provide an artificial hip joint prosthesis which can minimize interference and ensure its smooth rotation, thereby preventing the pelvis and femur of the human body from being injured.

Still another object of the present invention is to provide an artificial hip joint prosthesis which allows assembly and disassembly of component parts to be easily performed and which minimizes radial movement of a rotating head so that collision does not occur between the component parts and drawbacks associated with abrasion and wear of the component parts are not caused, while release of the head is properly prevented.

Yet still another object of the present invention is to provide an artificial hip joint prosthesis which is less complex to manufacture while maintaining structural integrity, thus reducing manufacturing costs.

In order to accomplish the above objects, the present invention provides an artificial hip joint prosthesis installed between a pelvis and a femur to allow the femur to be rotated relative to the pelvis, comprising: a pelvis-contacting element fixed to the pelvis and having a truncated hollow sphere-shaped configuration; a stem fixed to the femur; a head integrally coupled to a distal end of the stem and having a truncated sphere-shaped configuration; and a flexible joint member interposed between the pelvis-contacting element and the stem to accommodate and rotatably support the head, the flexible joint member capable of being resiliently deformed outward and inward in a radial direction to be coupled to and decoupled from the pelvis-contacting element along with the head.

Here, the flexible joint member may comprise a body part having a configuration of a hollow hemisphere; a resilient part formed at an entrance of the body part to have a predetermined thickness, the resilient part possessing a ring-shaped configuration; and a depressed part (also known hereinafter as a middle part) depressed radially inward by a predetermined depth between the body part and the resilient part to extend at least partially in a circumferential direction.

At this time, for providing proper elasticity to the resilient part, it is preferred that the depressed part is formed on an outer surface of the flexible joint member to have the predetermined depth and extends in the circumferential direction.

At least one through-hole is defined through the depressed part. The through-hole is defined in the form of a slot which is rounded at both ends thereof so that cracks are not formed in the depressed part due to a stress generated in the through-hole when the resilient part undergoes contraction and expansion. Also, it is preferred that a pair of through-holes are defined through the depressed part such that they are opposite to each other.

A pair of slits are defined in the resilient part at regions corresponding to the through-holes, such that the resilient part is divided into a pair of unit resilient portions which are separated by a predetermined distance and symmetrical with each other.

A pair of flattened portions are formed on an outer surface of the resilient part at regions corresponding to the slits each to extend through a predetermined angle in the circumferential direction.

Preferably, a pair of decoupling grooves are defined on the outer surface of the resilient part to be aligned on a line which is orthogonal to another line connecting the slits and thereby spaced apart from the slits by 90° in the circumferential direction, so that the flexible joint member can be decoupled from the pelvis-contacting element by pressing radially inward the resilient part in the decoupling grooves. The pair of decoupling grooves serve as tool passage openings so that a tool can be placed between the pelvis-contacting element and the flexible joint member when the flexible joint member is coupled to the pelvis-contacting element.

Projecting ribs are formed on one of an inner surface of the pelvis-contacting element and the outer surface of the resilient part, and engaging grooves in which the projecting ribs are to be engaged are defined on the other of the inner surface of the pelvis-contacting element and the outer surface of the resilient part. By this feature, it is possible to securely couple the pelvis-contacting element and the flexible joint member with each other.

At this time, it is preferred that the projecting ribs project radially outward from the outer surface of the resilient part and extend in the circumferential direction, and the engaging grooves are defined adjacent to an entrance of and on the inner surface of the pelvis-contacting element and have a preselected depth.

In order for ensuring easy decoupling of the flexible joint member from the pelvis-contacting element, it is preferred that each projecting rib is formed in a manner such that its height is gradually decreased from the decoupling groove toward the slit.

Each projecting rib has a first inclined surface which is inclined downward by a preselected angle when viewed in a direction where the flexible joint member is inserted into the pelvis-contacting element. By this feature, the flexible joint member can be inserted into the pelvis-contacting element with reduced force.

The resilient part is formed to have an outer diameter which is greater than a diameter of the entrance of the pelvis-contacting element, whereby the resilient part is prevented from being released after being inserted into the pelvis-contacting element. The resilient part is formed to have an inner diameter which is less than a diameter of the head, whereby unintentional release of the head from the resilient part is prevented.

An inner edge of each unit resilient portion is formed with a second inclined surface which has an inclination substantially corresponding to a surface curvature of the head to allow easy insertion and removal of the head into and out of the flexible joint member.

A pair of indented portions are defined on an inner surface of the flexible joint member in a manner such that they are diametrically opposite to each other and define a diameter which is greater than the diameter of the head, to ensure smooth insertion and removal of the head into and out of the flexible joint member. The indented portions create spaces of a predetermined size between the flexible joint member and the head when the head is inserted into the flexible joint member. When the flexible joint member is inserted along with the head into the pelvis-contacting element, the indented portions are biased radially inward so that the spaces created between the flexible joint member and the head are removed, to thereby appropriately support the head while preventing the head from being unintentionally released from the flexible joint member.

The flexible joint member has an inner diameter which corresponds to the diameter of the head, to minimize abrasion and wear of the component parts due to collision.

Meanwhile, a plurality of through-holes may be defined through the depressed part in a manner such that they are spaced apart one from another by a predetermined interval. In another embodiment of the present invention, the through-hole may not be defined in the form of a slot so long as a space for ensuring resilient deformation of the resilient part is provided in the flexible joint member and a dummy portion for additionally supporting the head inserted into the flexible joint member is produced in the depressed part.

In still another embodiment of the present invention, it can be envisaged that the projecting ribs project radially inward adjacent to the entrance of and from the inner surface of the pelvis-contacting element and have the preselected depth, and the engaging grooves are defined on the outer surface of the resilient part and extend in the circumferential direction.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE INVENTION

Figure 1:
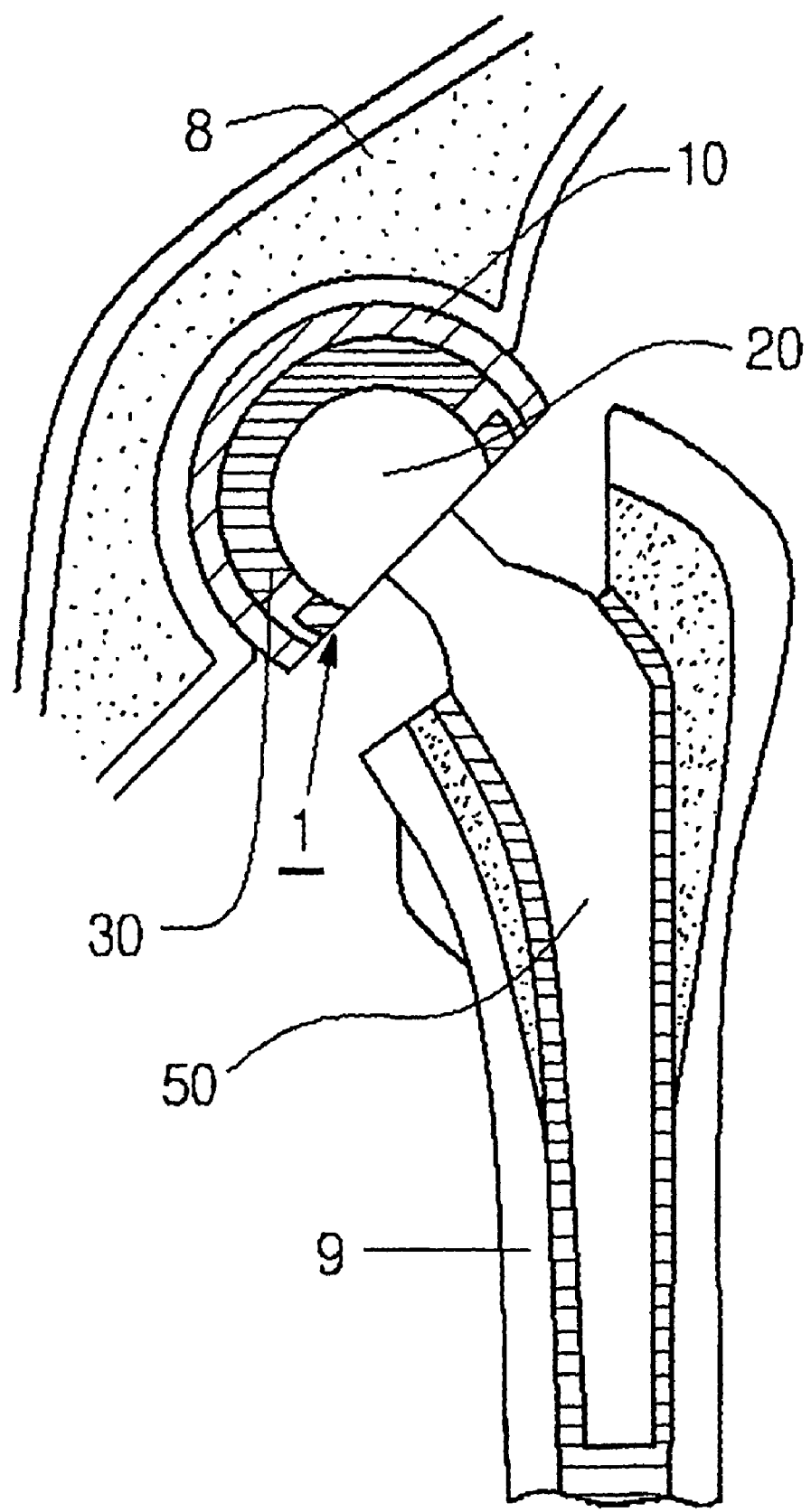
FIG. 1 is a view schematically illustrating a state wherein an artificial hip joint prosthesis in accordance with a first embodiment of the present invention is installed.

Reference should now be made to the drawings, in which the same reference numerals are used throughout the different drawings to designate the same or similar component parts. Hereafter, a first embodiment representative of the present invention will be described in detail, and as for the other embodiments, only the features which are different from those of the first embodiment will be described.

As shown in FIG. 1, an artificial hip joint prosthesis 1 in accordance with a first embodiment of the present invention is installed between a pelvis 8 and a femur 9 to connect the femur 9 to the pelvis 8 so that the femur 9 can be rotated relative to the pelvis 8.

Figure 2:
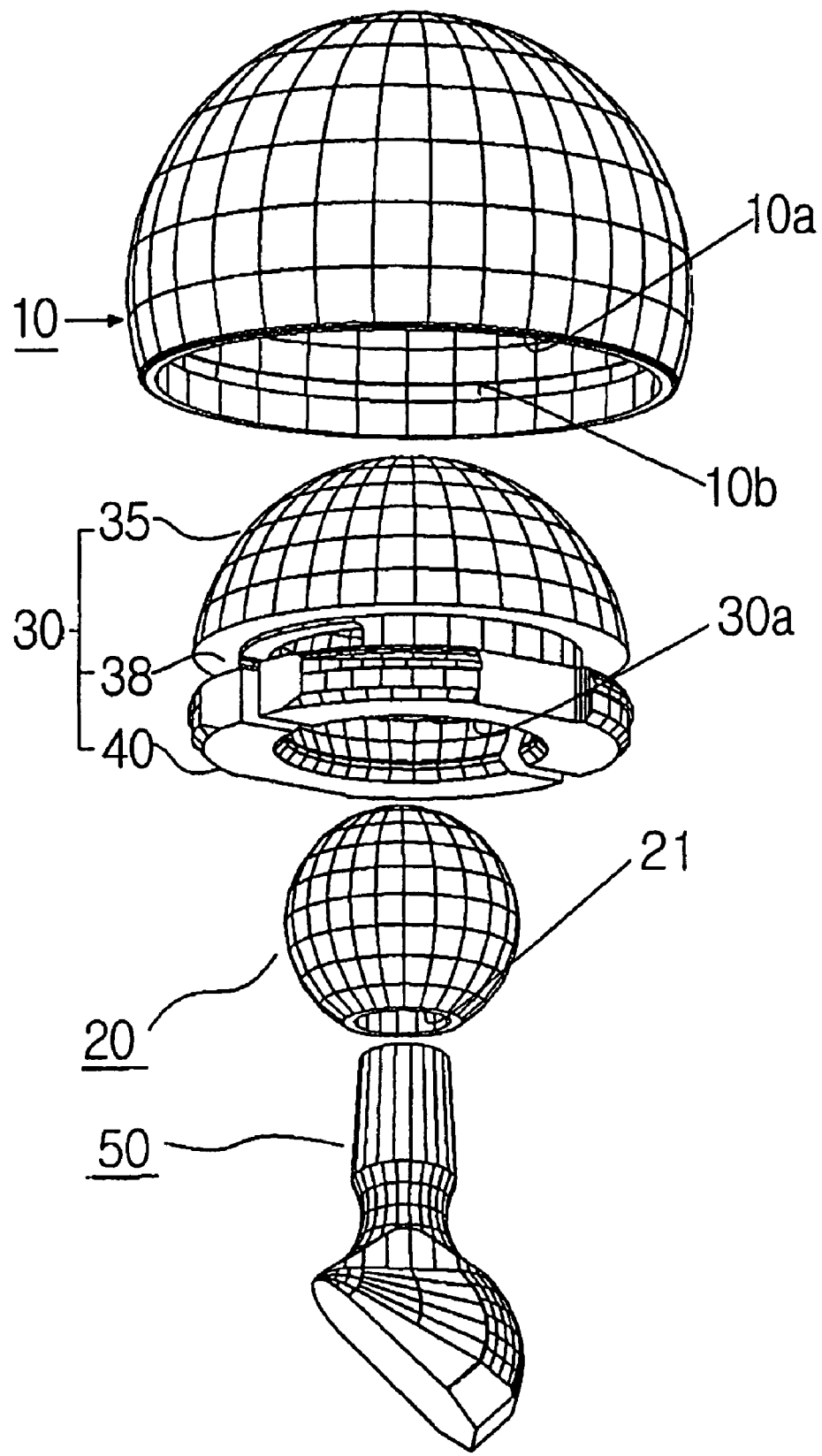
FIG. 2 is an exploded perspective view of the artificial hip joint prosthesis shown in FIG. 1.
Figure 3:
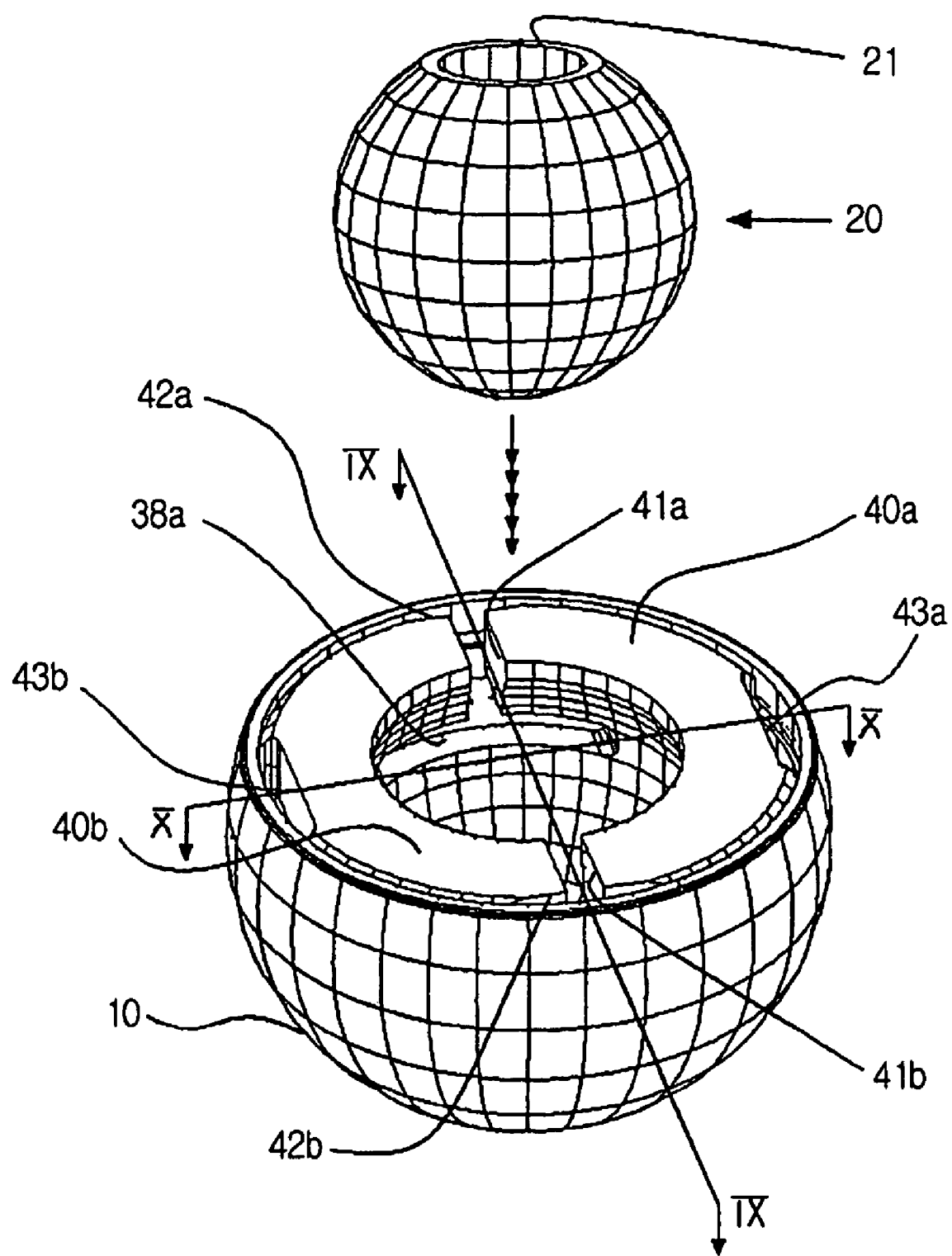
FIG. 3 is a perspective view illustrating a partially assembled state of the artificial hip joint prosthesis shown in FIG. 2.
Figure 4:
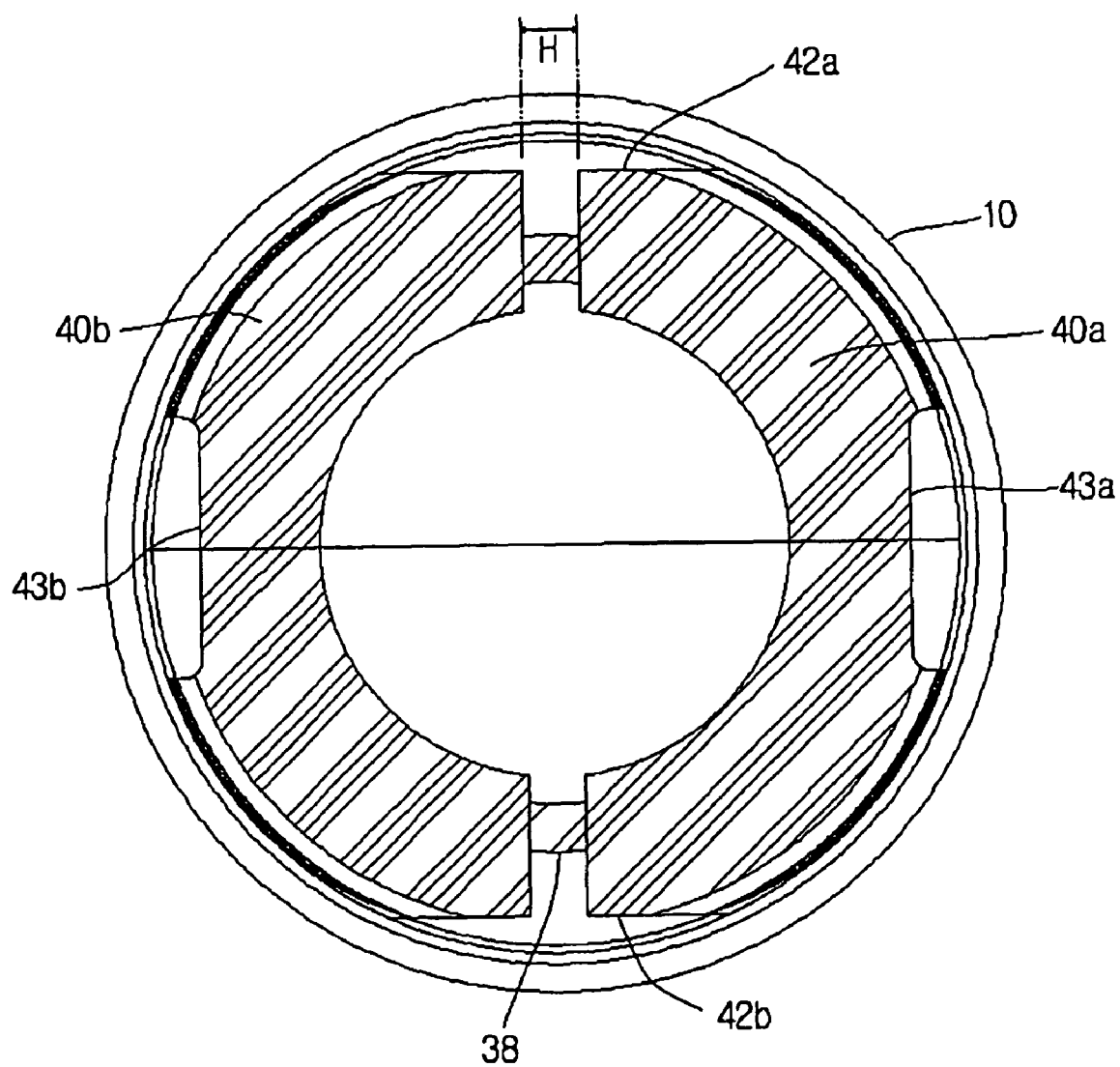
FIG. 4 is a plan view illustrating a state wherein a pelvis-contacting element and a flexible joint member are assembled with each other.
Figure 5:
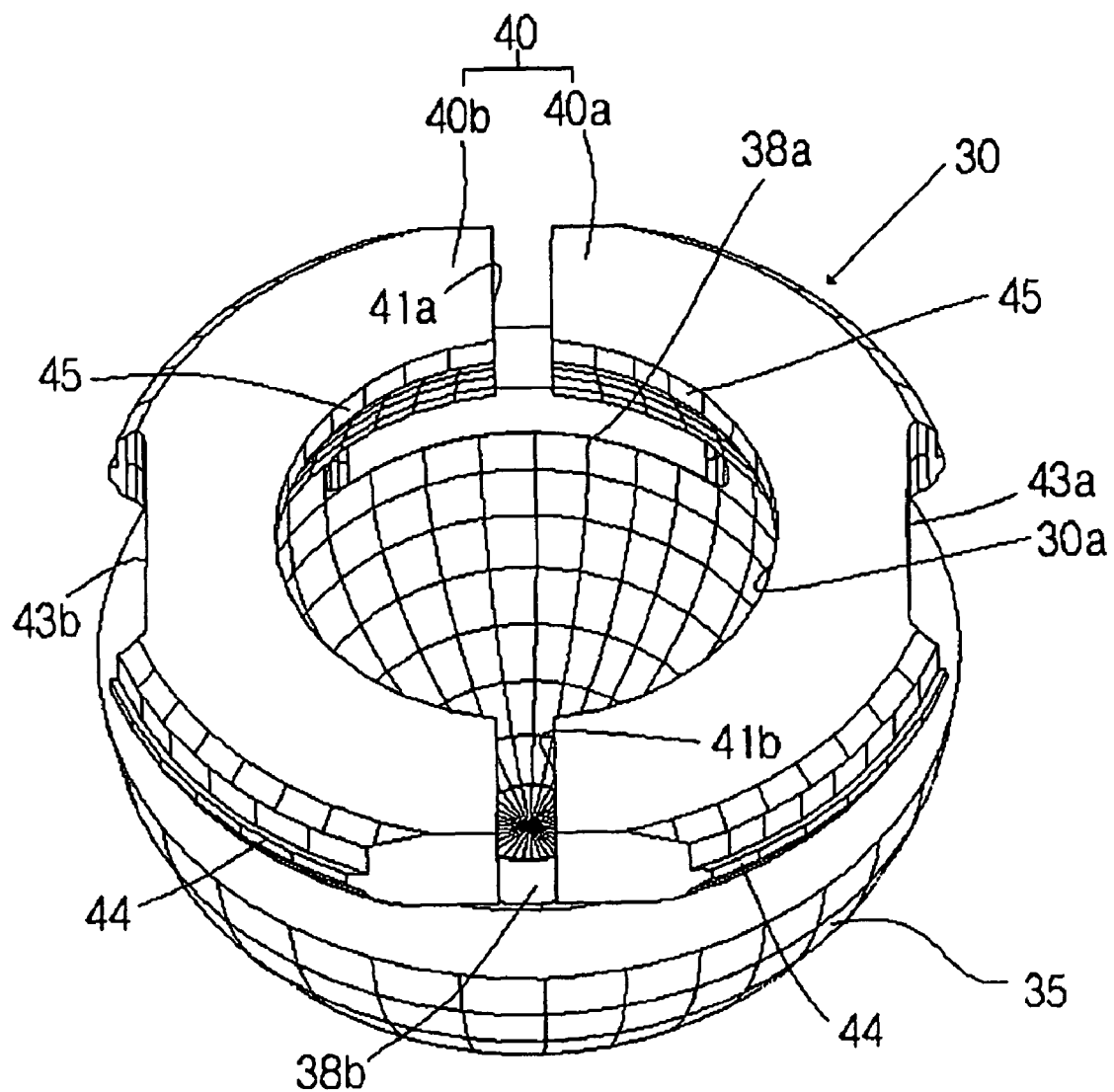
FIG. 5 is an enlarged perspective view of the flexible joint member.
Figure 6:
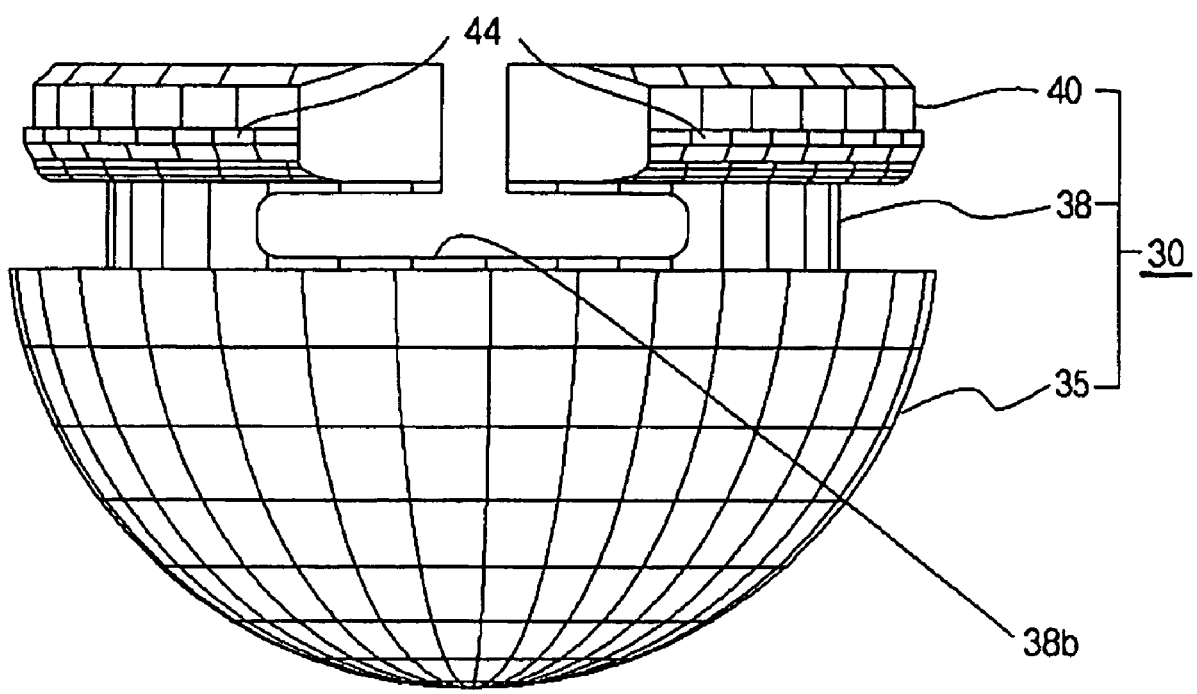
FIG. 6 is a side view of FIG. 5.

As can be readily seen from FIGS. 2 through 4, the artificial hip joint prosthesis 1 comprises a pelvis-contacting element 10 and a stem 50 which are respectively fixed to the pelvis 8 and the femur 9, and a flexible joint member 30 which is interposed between the pelvis-contacting element 10 and the stem 50 to rotatably connect the pelvis-contacting element 10 and the stem 50 with each other.

The pelvis-contacting element 10 may be formed of a metallic material, for example, stainless steel, alloyed steel, etc. The pelvis-contacting element 10 is formed to have a configuration of a truncated hollow sphere which has a volume slightly greater than that of a hollow hemisphere. The pelvis-contacting element 10 is inserted into the pelvis 8 in a manner such that an entrance 10a thereof faces the femur 9.

Figure 7:
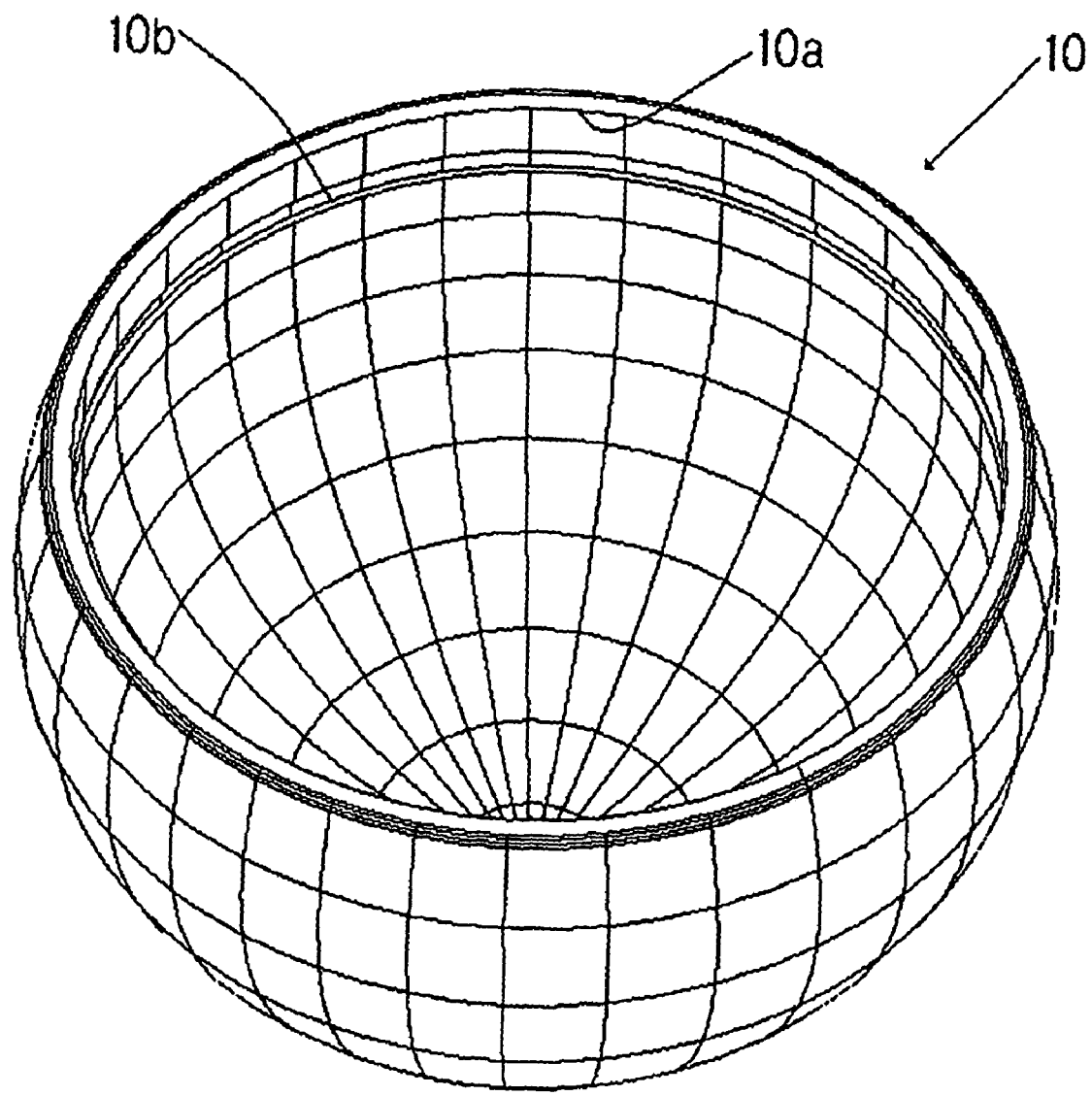
FIG. 7 is an enlarged perspective view of the pelvis-contacting element.
Figure 8:
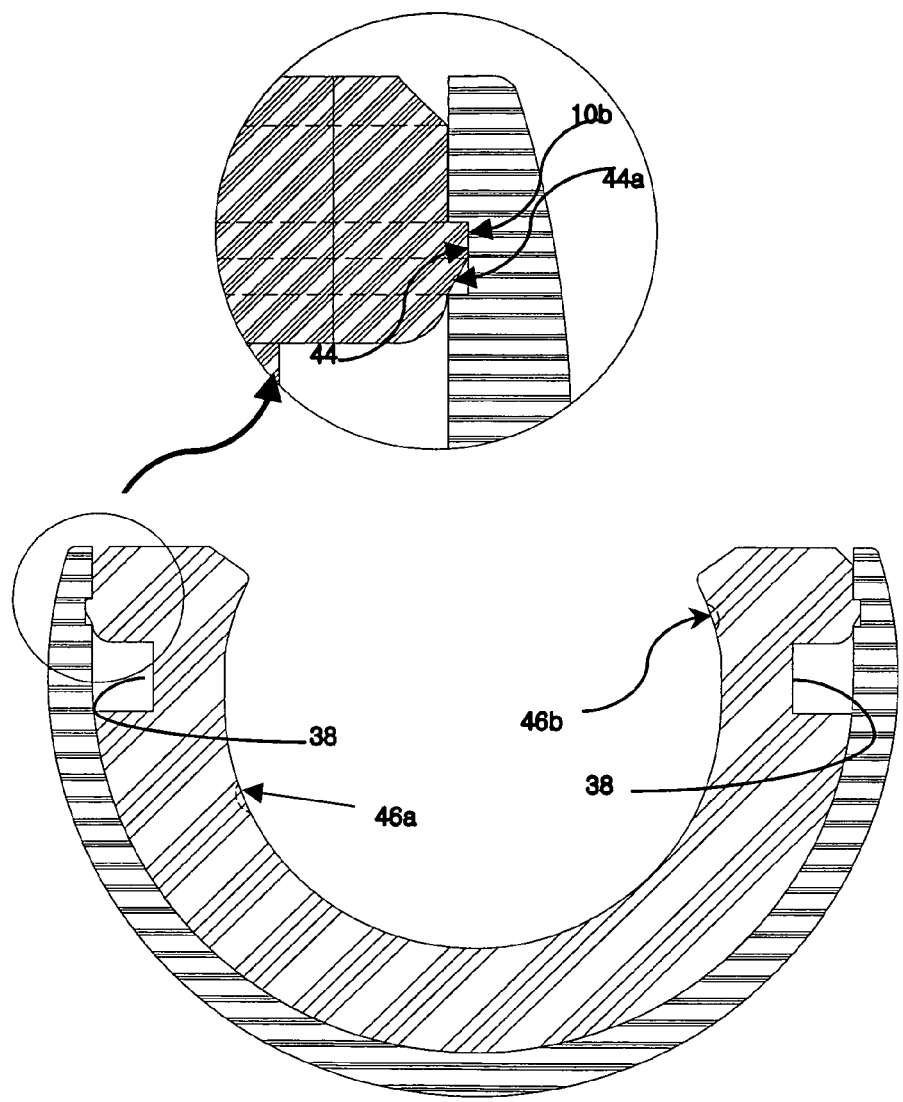
FIG. 8 is a partially enlarged schematic sectional view illustrating a state wherein the pelvis-contacting element and the flexible joint member are assembled with each other.
Figure 9:
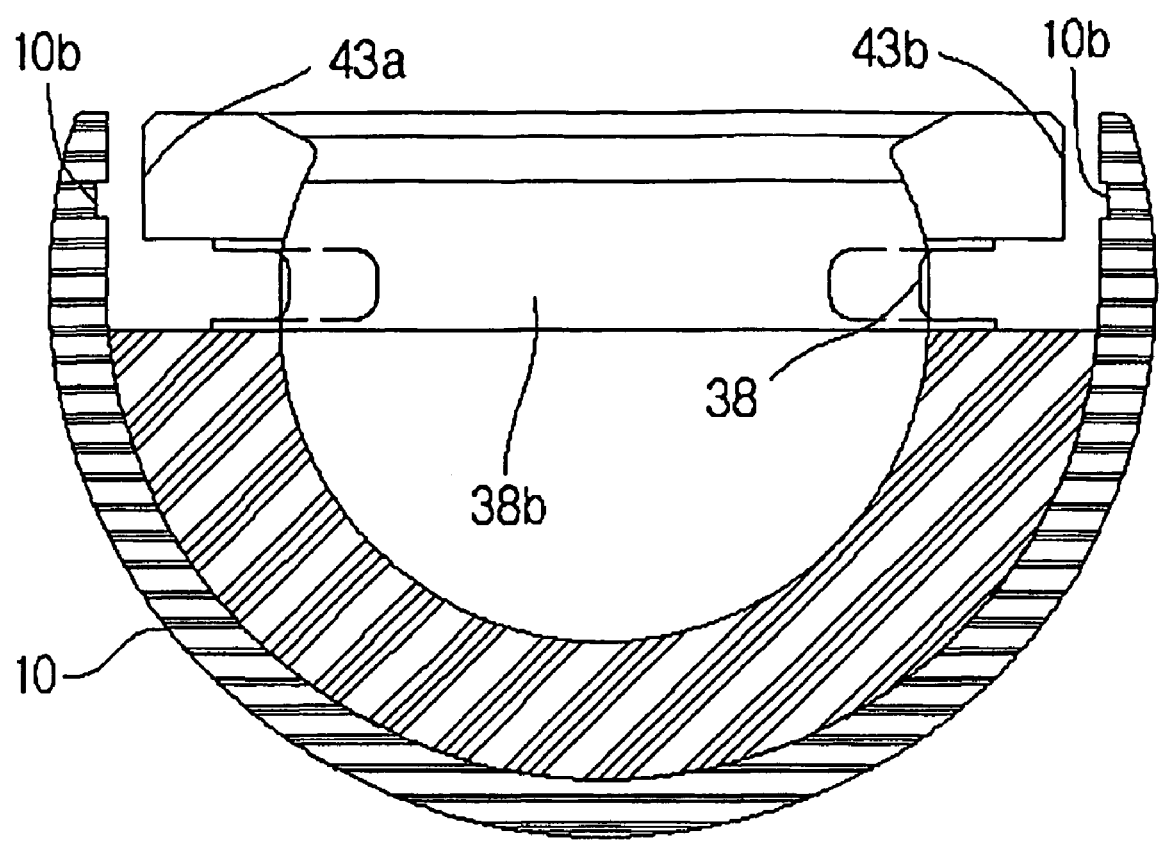
FIG. 9 is a sectional view taken along the line IX—IX of FIG. 3.
Figure 10:
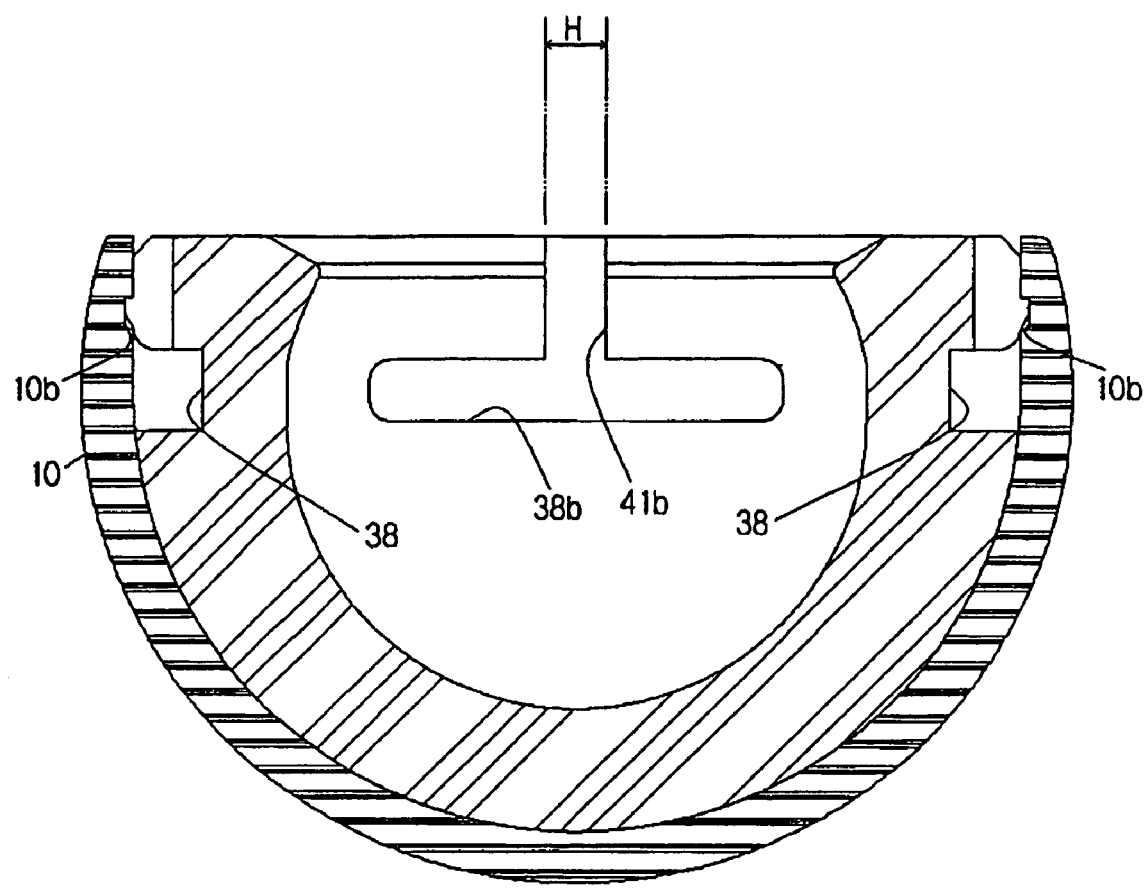
FIG. 10 is a sectional view taken along the line X—X of FIG. 3.

Engaging grooves 10b (see FIG. 7) in which projecting ribs 44 of the flexible joint member 30 are to be engaged, as will be described later in detail, are defined on an inner surface of the pelvis-contacting element 10 to have a preselected depth. The engaging grooves 10b are positioned adjacent to the entrance 10a between the entrance 10a and a center of the pelvis-contacting element 10.

The entrance 10a of the pelvis-contacting element 10 is formed to have an inner diameter which is less than a diameter of the flexible joint member 30, so that the flexible joint member 30 accommodated in the pelvis-contacting element can be prevented from being unintentionally released. Due to the fact that a height of the pelvis-contacting element 10 which is measured from the entrance 10a is less than a diameter of the pelvis-contacting element 10, it is possible to decrease a relative height of the flexible joint member 30. As a consequence, it is possible to manufacture an artificial hip joint prosthesis which can be adapted even to Orientals having relatively small physiques and bone sizes, install the artificial hip joint prosthesis in an easy and convenient manner, and shorten an installation time. Further, as will be described later in detail, since smooth rotation of the head 20 is ensured and interference between the pelvis-contacting element 10 and the head 20 is minimized, it is possible to prevent the pelvis including a cartilage and the femur of the human body from being injured.

The stem 50 has a long rod-shaped configuration and is fixed to the femur 9 along a lengthwise direction thereof. The stem 50 is integrally coupled at a distal end thereof with the head 20 which is to be inserted into the flexible joint member 30. The head 20 has a truncated sphere-shaped configuration to be freely rotated in the flexible joint member 30. The head 20 is defined with a hole 21 in which the distal end of the stem 50 is press-fitted.

The flexible joint member 30 can be resiliently deformed in radial inward and outward directions. As a consequence, the flexible joint member 30 can accommodate therein and support the head 20 so that the head 20 can be freely rotated, and can be coupled to and decoupled from the pelvis-contacting element 10 along with the head 20.

An outer surface of the flexible joint member 30 is contoured in conformity with the inner surface of the pelvis-contacting element 10 to be in surface contact therewith. The flexible joint member 30 has a resilient part 40 formed at an entrance thereof. The resilient part 40 has a diameter which is greater than the inner diameter of the entrance 10a of the pelvis-contacting element 10. By this fact, after the flexible joint member 30 is accommodated in the pelvis-contacting element 10 with the resilient part 40 resiliently contracted radially inward, the resilient part 40 can be resiliently expanded again radially outward to prevent the flexible joint member 30 from being unintentionally released from the pelvis-contacting element 10.

As can be readily seen from FIGS. 5 through 10, the flexible joint member 30 comprises a body part 35, the resilient part 40, and the depressed part 38 (also known hereinafter as a middle part). The body part 35 has a configuration of a hollow hemisphere. The resilient part 40 is formed at the entrance 30a of the body part 35 to have a predetermined thickness and possesses a ring-shaped configuration. The depressed part 38 is depressed radially inward on the outer surface of the flexible joint member 30 by a predetermined depth to extend at least partially in a circumferential direction between the body part 35 and the resilient part 40.

In this first embodiment of the present invention, the depressed part 38 is formed on the outer surface of the flexible joint member 30 in such a way as to continuously extend along the circumferential direction of the flexible joint member 30. At this time, it is preferable to determine a depth of the depressed part 38 so that the resilient part 40 can be reliably supported by the body part 35 and the flexible joint member 30 does not lose its resiliency even though it is repeatedly contracted and expanded.

A pair of through-holes 38a and 38b are defined through the depressed part 38 each to extend at least partially in the circumferential direction. Each of the through-holes 38a and 38b is defined in the form of a slot which is rounded at both ends thereof so that cracks are not formed in the depressed part 38 due to repeated contraction and expansion. The pair of through-holes 38a and 38b are defined through the depressed part 38 such that they are opposite to each other. The through-holes 38a and 38b are not necessarily defined in the depressed part 38.

In order to ensure that the flexible joint member 30 is resiliently deformed in an easy manner while the flexible joint member 30 accommodates the head 20 or is inserted by itself into the pelvis-contacting element 10, the resilient part 40 is divided into a pair of unit resilient portions 40a and 40b which are separated by a predetermined distance H and symmetrical with each other. The pair of unit resilient portions 40a and 40b are formed by the fact that a pair of slits 41a and 41b are defined in the resilient part 40 at regions where the through-holes 38a and 38b are respectively defined.

A pair of flattened portions 42a and 42b are formed on an outer surface of the resilient part 40 at regions where the slits 41a and 41b are respectively defined, so that each of the flattened portions 42a and 42b extends through a predetermined angle in the circumferential direction. The flattened portions 42a and 42b are formed to ensure that the pair of unit resilient portions 40a and 40b can be biased toward each other by a small level of force.

In cooperation with the material used for forming the flexible joint member 30 which may be, for example, silicon, ceramic and thermoplastic synthetic resin, the depressed part 38, the through-holes 38a and 38b and the slits 41a and 41b play an important role of determining a flexibility of the flexible joint member 30 which repeatedly undergoes contraction and expansion. If the flexible joint member 30 has excessive flexibility, coupling of the flexible joint member 30 with the head 20 and the pelvis-contacting element 10 can be easily effected, but the likelihood of the flexible joint member 30 to be released therefrom is increased. On the contrary, if the flexible joint member 30 has insufficient flexibility, coupling of the flexible joint member 30 with the head 20 and the pelvis-contacting element 10 cannot be easily effected. Accordingly, the depressed part 38, the through-holes 38a and 38b and the slits 41a and 41b must be defined to have appropriate contours and sizes.

With the flexible joint member 30 coupled to the pelvis-contacting element 10, in order to allow the flexible joint member 30 to be decoupled from the pelvis-contacting element 10, a pair of decoupling grooves 43a and 43b are defined on the outer surface of the resilient part 40.

The pair of decoupling grooves 43a and 43b are defined on the outer surface of the resilient part 40 in a manner such that they are aligned on a line which is orthogonal to another line connecting the slits 41a and 41b with each other and thereby are spaced apart from the slits 41a and 41b by 90° in the circumferential direction. The pair of decoupling grooves 43a and 43b serve as tool passage openings so that a tool can be placed between the pelvis-contacting element 10 and the flexible joint member 30 when the flexible joint member 30 is coupled to the pelvis-contacting element 10. Actually, when performing an operation, as occasion demands, decoupling of the head 20 formed at the distal end of the stem 50 from the flexible joint member 30 or decoupling of the flexible joint member 30 having the head 20 inserted therein from the pelvis-contacting element 10 may be needed or not. In consideration of this fact, in a fifth embodiment of the present invention, the pair of decoupling grooves 43a and 43b may be or may not be defined on the outer surface of the resilient part 40.

If the flexible joint member 30 can be easily decoupled from the pelvis-contacting element 10, when performing an operation, convenience can be improved and a required time can be shortened. Therefore, it is preferred that the decoupling grooves 43a and 43b are normally defined on the outer surface of the resilient part 40.

Here, the tool for decoupling the flexible joint member 30 from the pelvis-contacting element 10 may have a configuration such as of a pair of long-nose pliers. In this case, after placing the respective actuating arms of the pliers into the pair of decoupling grooves 43a and 43b, by pressing grip portions of the pliers toward each other, the flexible joint member 30 can be easily decoupled from the pelvis-contacting element 10. If a tool is not separately prepared, the flexible joint member 30 can be decoupled from the pelvis-contacting element 10 using two screwdrivers.

The projecting ribs 44 are formed in a manner such that they project radially outward from the outer surface of the resilient part 40 and extend in the circumferential direction of the resilient part 40. When the flexible joint member 30 is accommodated in the pelvis-contacting element 10, the projecting ribs 44 are engaged into the engaging grooves 10b which are defined on the inner surface of the pelvis-contacting element 10.

When it is necessary to decouple the flexible joint member 30 from the pelvis-contacting element 10, by pressing the resilient part 40 radially inward in the decoupling grooves 43a and 43b using a separate tool, the resilient part 40 is contracted along the circumferential direction. At this time, in the regions where the slits 41a and 41b are defined to divide the resilient part 40 into the pair of unit resilient portions 40a and 40b, since contraction occurs to a slight extent, it is not easy to decouple the flexible joint member 30 from the pelvis-contacting element 10.

Figure 11:
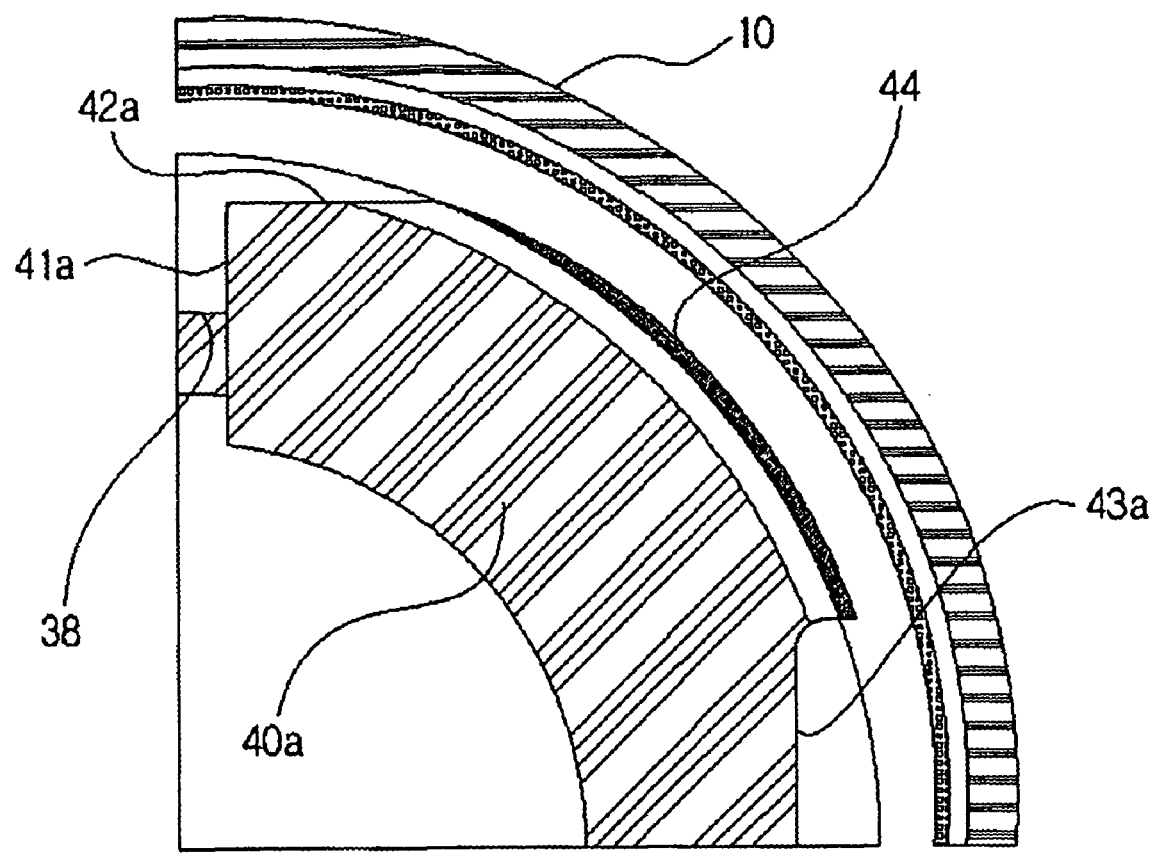
FIG. 11 is a transverse sectional view illustrating a main part of FIG. 3.

To cope with this problem, as shown in FIG. 11, the projecting ribs 44 are formed in a manner such that their height is gradually decreased from the decoupling grooves 43a and 43b toward the slits 41a and 41b. Due to this fact, in the regions where the slits 41a and 41b are defined in the resilient part 40 and contraction occurs to a slight extent, the projecting ribs 44 can be easily disengaged from the engaging grooves 10b.

Each projecting rib 44 has a first inclined surface 44a which is inclined downward by a preselected angle when the surface 44a is viewed in a direction along which the flexible joint member 30 is inserted into the pelvis-contacting element 10. Thus, when the flexible joint member 30 is inserted into the pelvis-contacting element 10, due to the presence of the first inclined surface 44a, the flexible joint member 30 can be slidingly guided at the entrance 10a of the pelvis-contacting element 10. Thereafter, the projecting ribs 44 are respectively engaged into the engaging grooves 10b. At this time, after the engagement is effected between the projecting ribs 44 and the engaging grooves 10b, the projecting ribs 44 are respectively brought into contact with bottom surfaces of the engaging grooves 10b in a vertical direction, whereby the flexible joint member 10 is prevented from being unintentionally released in a direction opposite to the direction along which the flexible joint member 30 is inserted into the pelvis-contacting element 10 (see the enlarged part in FIG. 8).

The resilient part 40 which is divided into the pair of unit resilient portions 40a and 40b is formed to have an outer diameter which is greater than a diameter of the entrance 10a of the pelvis-contacting element 10. By this fact, when the flexible joint member 30 is accommodated in the pelvis-contacting element 10, the pair of unit resilient portions 40a and 40b are contracted radially inward, and the projecting ribs 44 are inserted and engaged into the engaging grooves 10b, respectively. When the insertion of the projecting ribs 44 into the engaging grooves 10b is completed, the pair of unit resilient portions 40a and 40b are expanded radially outward so that the projecting ribs 44 can be held securely engaged in the engaging grooves 110b.

Further, the resilient part 40, which is divided into the pair of unit resilient portions 40a and 40b, is formed to have an inner diameter which is less than a diameter of the head 20. By this fact, when the head 20 is accommodated in the flexible joint member 30, the pair of unit resilient portions 40a and 40b are expanded radially outward. When the insertion of the head 20 into the flexible joint member 30 is completed, the pair of unit resilient portions 40a and 40b are contracted radially inward to properly support the head 20. At this time, an inner edge of each unit resilient portion 40a and 40b is formed with a second inclined surface 45, which has an inclination substantially corresponding to a surface curvature of the head 20 to allow easy insertion and removal of the head into and out of the flexible joint member 30.

While the flexible joint member 30 is formed to have the diameter which is substantially the same as the diameter of the head 20 so that collision does not occur between the component parts and abrasion and wear are not caused, a pair of indented portions 46a and 46b are defined on an inner surface of the flexible joint member 30 in a manner such that they define a diameter which is greater than the diameter of the head 20, to ensure smooth insertion and removal of the head 20 into and out of the flexible joint member 30. The pair of indented portions 46a and 46b are defined to be diametrically opposite to each other.

The indented portions 46a and 46b (see FIG. 8, where the dotted lines show the indented portions when the flexible joint member 30 is not placed in the pelvis-contacting element 10) create spaces of a predetermined size between the flexible joint member 30 and the head 20 when the head 20 is inserted into the flexible joint member 30. When the flexible joint member 30 is inserted into the pelvis-contacting element 10 along with the head 20 accommodated therein, the indented portions 46a and 46b are biased radially inward. In this way, as the contraction is effected in the flexible joint member 30 having accommodated therein the head 20, the spaces created between the head 20 and the flexible joint member 30 due to the presence of the indented portions 46a and 46b are removed, whereby collision does not occur and the head 20 can be securely supported in the flexible joint member 30.

Hereinafter, a procedure for installing the artificial hip joint prosthesis 1 according to the present invention, constructed as mentioned above, will be described.

First, a position and a status of the pelvis 8 into which the pelvis-contacting element 10 is to be inserted are checked. Then, after fixing the stem 150 to the femur 9, the head 20 is coupled to the distal end of the stem 50.

Next, the head 20 coupled with the stem 50 is inserted through the entrance 30a of the flexible joint member 30. By doing this, as the head 20 is guided along the second inclined surface 45 which is formed on the inner edge of each unit resilient portion 40a and 40b, the head 20 is inserted into the flexible joint member 30 which is resiliently expanded outward in the radial direction.

That is to say, the pair of unit resilient portions 40a and 40b are expanded radially outward due to the presence of the depressed part 38, through-holes 38a and 38b and slits 41a and 41b which are formed on or defined in the flexible joint member 30. When the head 20 is completely inserted into the flexible joint member 30, the pair of unit resilient portions 40a and 40b are contracted radially inward.

By the fact that the pair of indented portions 46a and 46b are defined on the inner surface of the flexible joint member 30 in a manner such that they define the diameter which is greater than the diameter of the head 20, if the head 20 is completely inserted into the flexible joint member 30, the spaces of the predetermined size are created between the inner surface of the flexible joint member 30 and the outer surface of the head 20.

If the coupling of the head 20 with the flexible joint member 30 is completed, the flexible joint member 30 having accommodated therein the head is inserted into the pelvis-contacting element 10. Thereupon, due to the presence of the depressed part 38, through-holes 38a and 38b and slits 41a and 41b, the pair of unit resilient portions 40a and 40b are resiliently contracted radially inward, by which the flexible joint member 30 is inserted into the pelvis-contacting element 10. After the insertion of the flexible joint member 30 into the pelvis-contacting element 10 is completed, the pair of unit resilient portions 40a and 40b are expanded radially outward again.

At this time, the projecting ribs 44 are respectively engaged into the engaging grooves 10b. Since an expansion degree of the flexible joint member is less than a contraction degree thereof, if the flexible joint member 30 is completely inserted into the pelvis-contacting element 10, the spaces created between the outer surface of the head 20 and the inner surface of the flexible joint member 30 are removed. Consequently, the head 20 can be held securely supported in the flexible joint member 30, and at the same time, the flexible joint member 30 can be securely supported in the pelvis-contacting element 10. Thereafter, the combination of the head 20, flexible joint member 30 and pelvis-contacting element 10 which are coupled one with another is positioned in place on the pelvis 8.

As apparent from the above description, in the present invention, since it is possible to operatively connect the head 20 and the pelvis-contacting element with each other by virtue of resiliency of the flexible joint member 30 which comprises a single component which allows a user to easily and simply manipulate the joint member 30, it is possible to conveniently install the artificial hip joint prosthesis and shorten an installation time.

Further, in the present invention, because it is possible to decrease relative heights of the pelvis-contacting element 10 and the flexible joint member 30, the artificial hip joint prosthesis can be easily and conveniently adapted even to Orientals having relatively small physiques and bone sizes. Also, since smooth rotation of the head 20 is ensured and interference between the pelvis-contacting element 10 and the head 20 is minimized, it is possible to prevent the pelvis including a cartilage and the femur of the human body from being injured.

Moreover, in the present invention, the pelvis-contacting element 10, the head 20 and the flexible joint member 30 can be easily coupled to and decoupled from one another, and collision and interference between component parts are minimized. In addition, it is possible to prevent the respective component parts from being unintentionally released from one another. Because the flexible joint member 30 comprises a single component, manufacture of the artificial hip joint prosthesis can be conveniently implemented and a manufacturing cost can be reduced.

Figure 12:
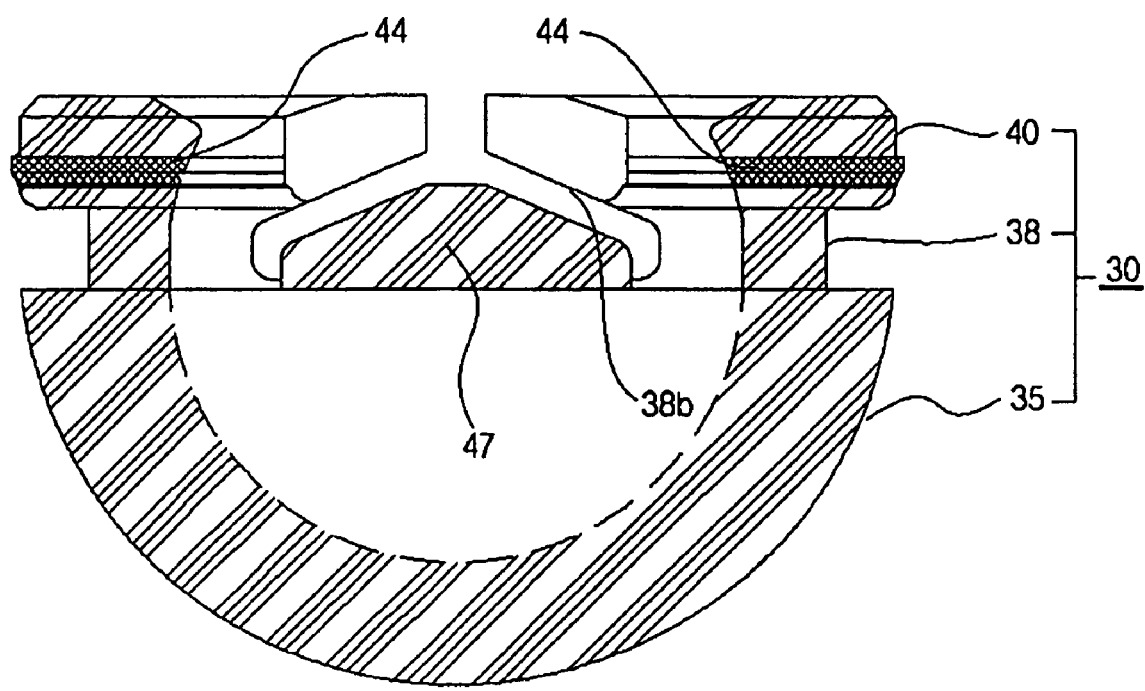
FIG. 12 is a side view similar to FIG. 6, illustrating a flexible joint member in accordance with a second embodiment of the present invention.

In the above-described embodiment, it was explained that the through-holes 38a and 38b of the flexible joint member 30 are defined in the form of a slot. However, as shown in FIG. 12, instead of defining the through-holes 38a and 38b in the form of a slot, the through-hole 38b can be defined in a manner such that a space for ensuring resilient deformation of the resilient part 40 is sufficiently provided in the flexible joint member 30 and a dummy portion 47 for additionally supporting the head 20 inserted into the flexible joint member 30 is formed on the depressed part 38.

Figure 13:
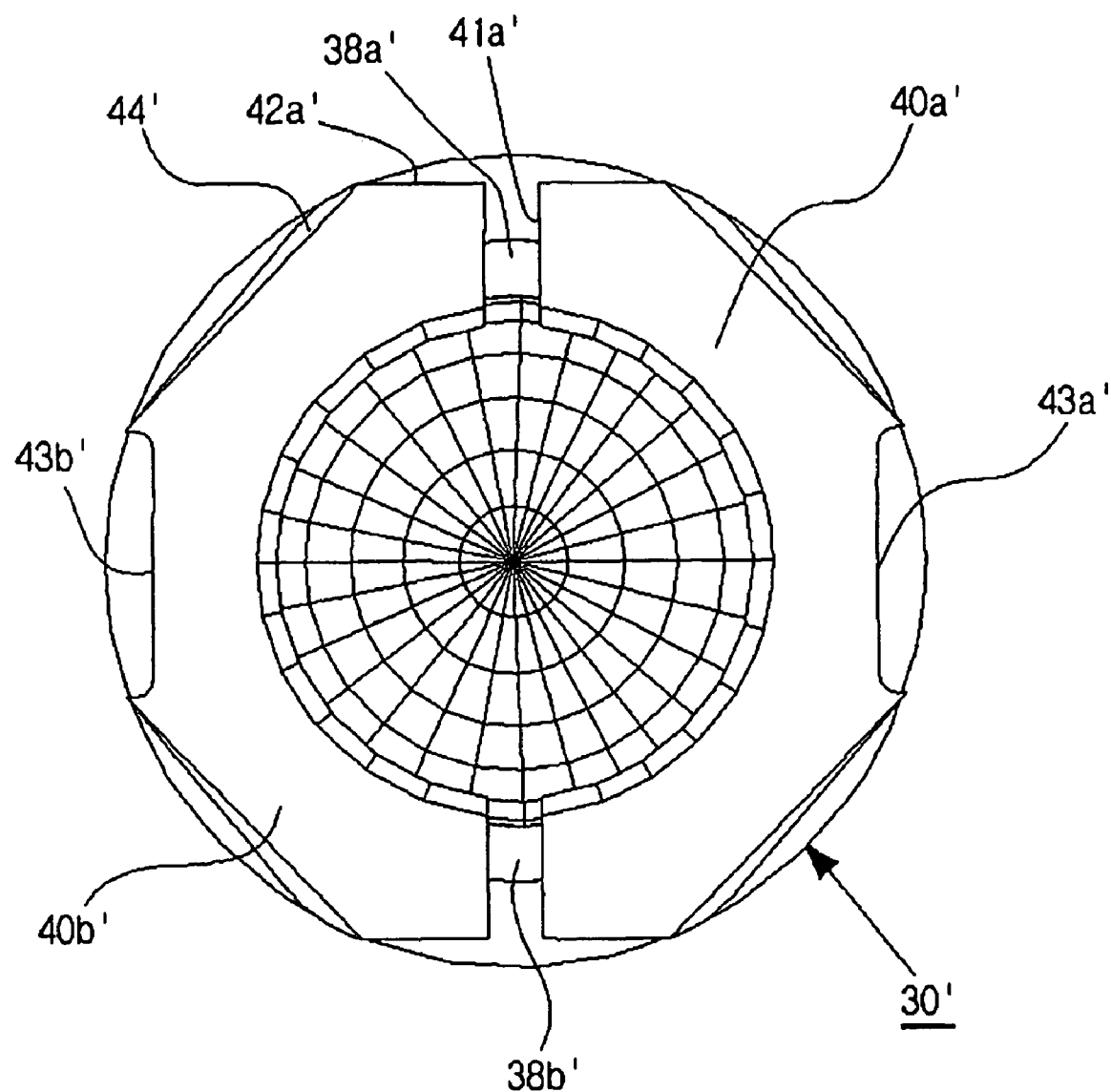
FIG. 13 is a plan view similar to FIG. 4, illustrating a flexible joint member in accordance with a third embodiment of the present invention.

Also, as shown in FIG. 13, the configuration of the flexible joint member 30' can be partially changed. In other words, the unit resilient portions 40a' and 40b' can be formed to have a polygonal configuration, and the associated parts such as the slits 41a' and 41b', the projecting ribs 44', the flattened portions 42a' and 42b' and the through-holes 38a' and 38b' can be defined or formed to have a corresponding contour or configuration.

Figure 14:
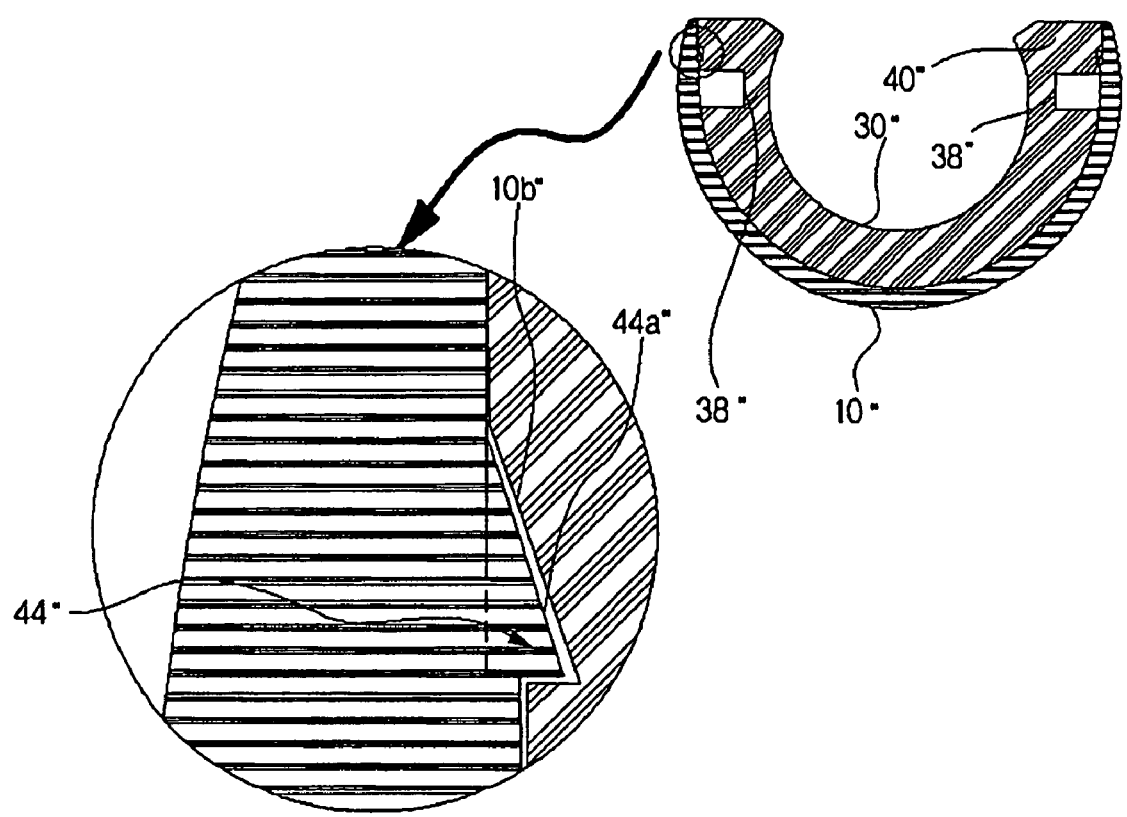
FIG. 14 is a partially enlarged schematic sectional view similar to FIG. 8, illustrating a state wherein a pelvis-contacting element and a flexible joint member in accordance with a fourth embodiment of the present invention are assembled with each other.

Furthermore, in the above-described embodiment, it was explained that the projecting ribs 44 are formed on the resilient part 40 and the engaging grooves 10b are defined in the pelvis-contacting element 10. However, in another embodiment of the present invention as shown in FIG. 14, the projecting ribs 44" can project radially inward adjacent to the entrance of and from the inner surface of the pelvis-contacting element 10" and have the preselected depth, and the engaging grooves 10b" can be defined on the outer surface of the resilient part 40" of the flexible joint member 30" and extend in the circumferential direction.

Figure 15:
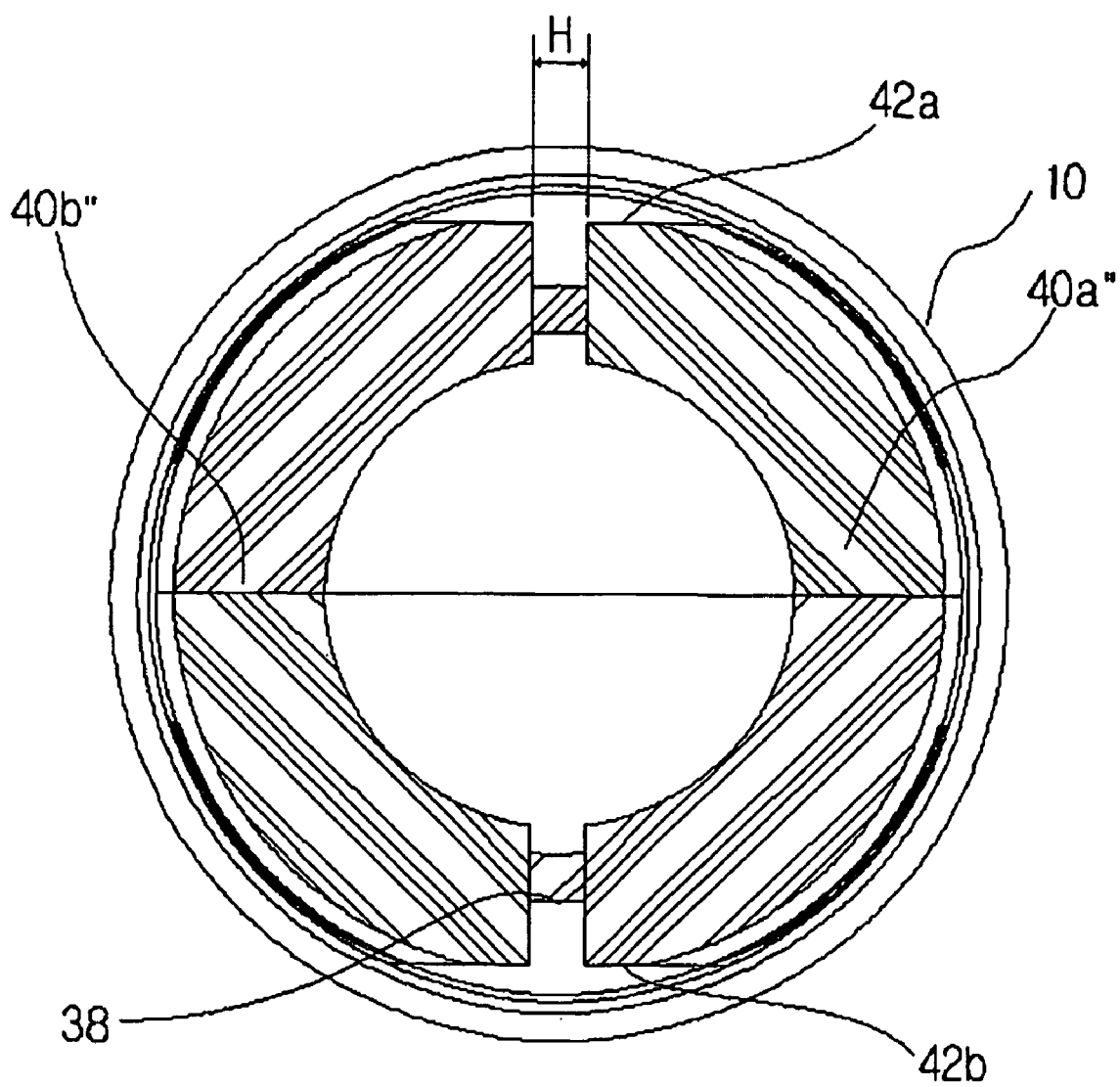
FIG. 15 is a plan view similar to FIG. 4, illustrating a state wherein a pelvis-contacting element and a flexible joint member in accordance with a fifth embodiment of the present invention are assembled with each other.
Figure 16:
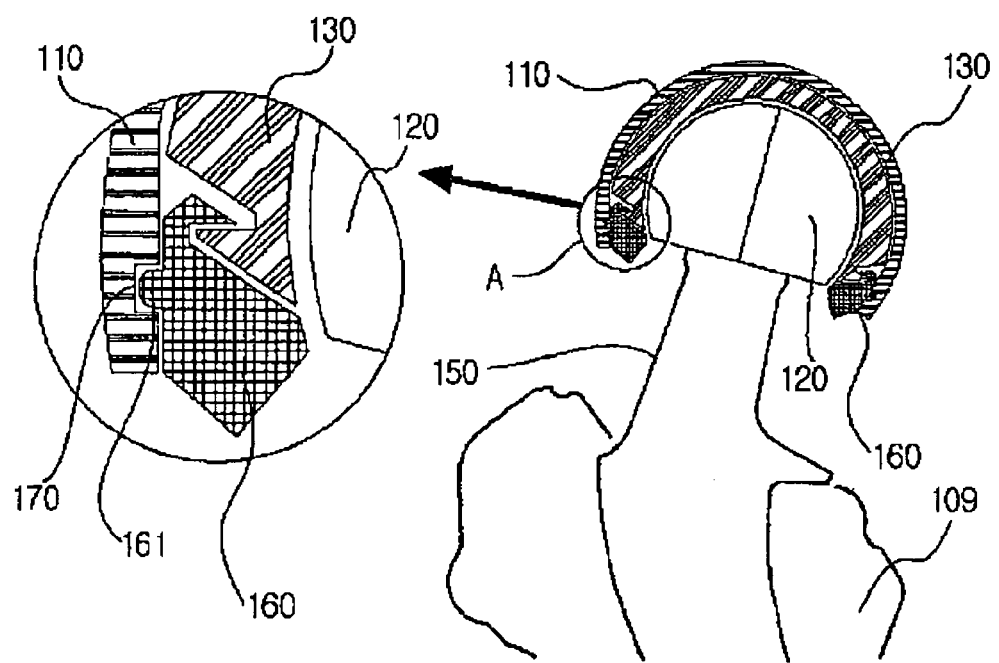
FIGS. 16 through 18 are views respectively illustrating the conventional artificial hip joint prostheses.
Figure 17:
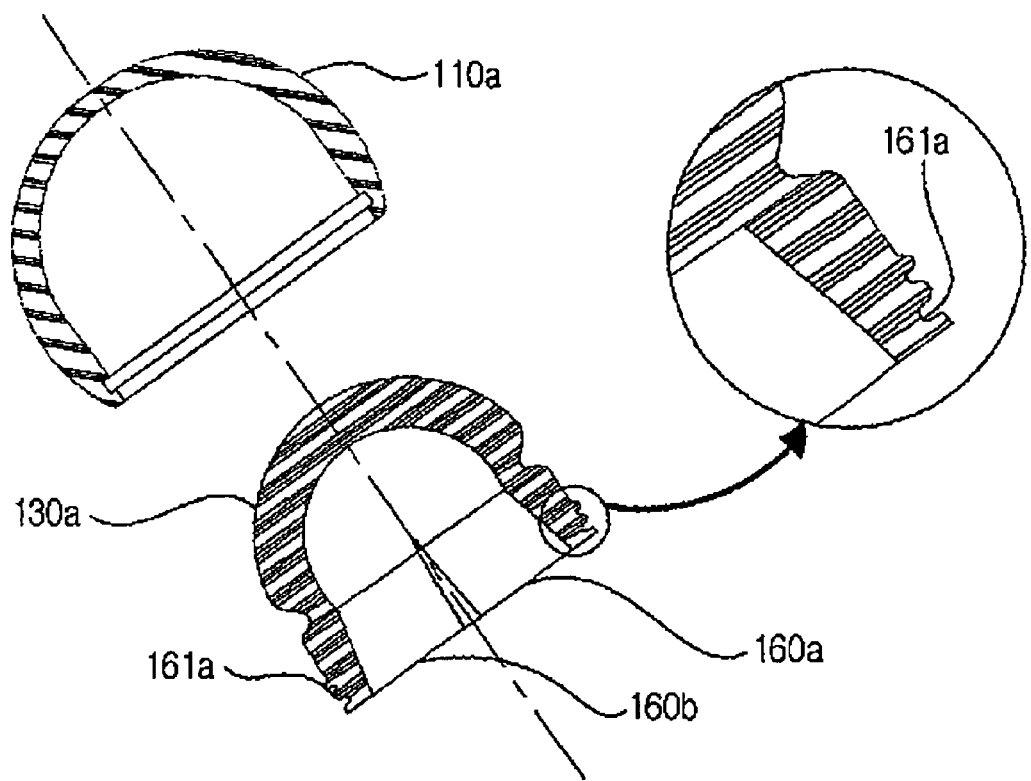
Figure 18:
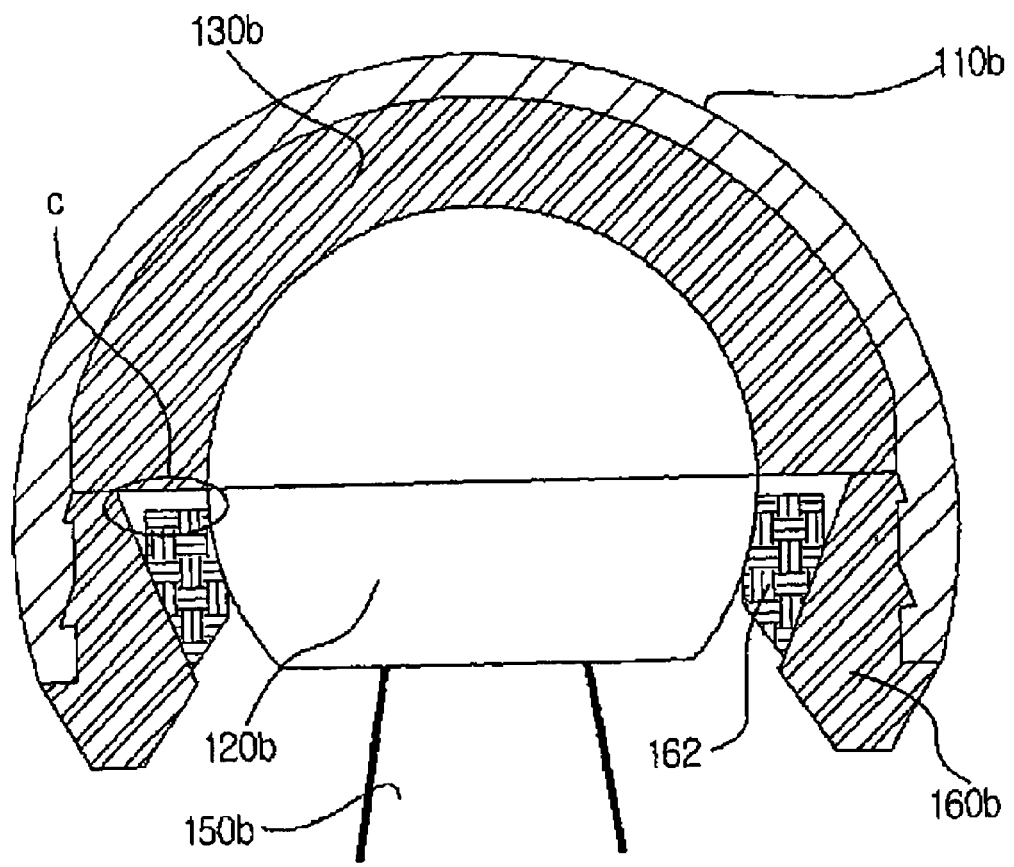

When selectively decoupling the head 20 and the stem 50 from their corresponding component elements, it is not always necessary to decouple the flexible joint member 30 from the pelvis-contacting element 10. Accordingly, as shown in FIG. 15, within the scope of the present invention, the decoupling grooves may not be defined in the unit resilient portions 40a''' and 40b''' of the flexible joint member 30.

INDUSTRIAL APPLICABILITY

As described above, the present invention provides an artificial hip joint prosthesis in which interference and collision are minimized between component parts and which ensures smooth rotation of a head and is constructed in such a way as to be easily installed and shorten an installation time.

The artificial hip joint prosthesis according to the present invention can be optimally adapted even to Orientals having relatively small physiques and bone sizes, and can minimize the interference and collision between the component parts to thereby prevent the pelvis including a cartilage and the femur of the human body from being injured.

The artificial hip joint prosthesis according to the present invention allows assembly and disassembly of component parts to be easily performed and minimizes radial movement of the head so that collision does not occur between the component parts, while release of the head is properly prevented. As the present artificial hip joint prosthesis is constructed to render partial structural integration, it is possible to simplify a manufacturing procedure and reduce a manufacturing cost.

The invention claimed is:

1. An artificial hip joint prosthesis for installation between a pelvis and a femur to allow the femur to be rotated relative to the pelvis, comprising:
   a pelvis-contacting element having a truncated hollow sphere-shaped configuration;
   a stem capable of being fixed to the femur;
   a head integrally coupled to a distal end of the stem and having a truncated sphere-shaped configuration; and
   a flexible joint member interposed between the pelvis-contacting element and the stem to accommodate and rotatably support the head, the flexible joint member comprising:

a body part having a configuration of a hollow hemisphere;

a substantially ring shaped resilient part formed at an entrance of the body part to have a predetermined thickness, the resilient part having at least one slit to allow expansion of the resilient part; and a middle part between the body part and the resilient part, the middle part having at least one through-hole that is wider than the slit in the resilient part, wherein a pair of indented portions are defined on an inner surface of the flexible joint member in a manner such that they are diametrically opposite to each other and help to define an inner diameter of the joint member which is greater than the diameter of the head coupled to the stem, to ensure smooth insertion and removal of the head into and out of the flexible joint member.

2. The artificial hip joint prosthesis according to claim 1, wherein the middle part is formed on an outer surface of the flexible joint member to have a predetermined depth and continuously extends along the circumferential direction.

3. The artificial hip joint prosthesis according to claim 1, wherein the through-hole comprises a slot which is rounded at both ends thereof.

4. The artificial hip joint prosthesis according to claims 1, wherein a pair of through-holes are defined such that they are opposite to each other.

5. The artificial hip joint prosthesis according to claim 4, wherein a pair of slits are defined in the resilient part at regions corresponding to the through-holes, such that the resilient part is divided into a pair of unit resilient portions which are separated by a predetermined distance and symmetrical with each other.

6. The artificial hip joint prosthesis according to claim 5, wherein a pair of flattened portions are formed on an outer surface of the resilient part at regions corresponding to the slits each to extend through a predetermined angle in the circumferential direction.

7. The artificial hip joint prosthesis according to claim 5, wherein a pair of decoupling grooves are defined on the outer surface of the resilient part to be aligned on a line which is orthogonal to another line connecting the slits and thereby spaced apart from the slits by 90 in the circumferential direction, so that the flexible joint member can be decoupled from the pelvis-contacting element by pressing radially inward the resilient part in the decoupling grooves.

8. The artificial hip joint prosthesis according to claim 7, wherein the pair of decoupling grooves serve as tool passage openings so that a tool can be placed between the pelvis-contacting element and the flexible joint member when the flexible joint member is coupled to the pelvis-contacting element.

9. The artificial hip joint prosthesis according to any one of the claims 1, 5 and 7, wherein projecting ribs are formed on one of an inner surface of the pelvis-contacting element and the outer surface of the resilient part, and engaging grooves in which the projecting ribs are to be engaged are defined on the other of the inner surface of the pelvis-contacting element and the outer surface of the resilient part.

10. The artificial hip joint prosthesis according to claim 9, wherein the projecting ribs project radially outward from the outer surface of the resilient part and extend in the circumferential direction, and the engaging grooves are defined adjacent to an entrance of and on the inner surface of the pelvis-contacting element and have a preselected depth.

11. The artificial hip joint prosthesis according to claim 10, wherein each projecting rib is formed in a manner such that its height is gradually decreased.

12. The artificial hip joint prosthesis according to claim 10, wherein each projecting rib has a first inclined surface which is inclined downward by a preselected angle when measured in a direction where the flexible joint member is inserted into the pelvis-contacting element.

13. The artificial hip joint prosthesis according to claim 5, wherein the resilient part is formed to have an outer diameter which is greater than a diameter of the entrance of the pelvis-contacting element.

14. The artificial hip joint prosthesis according to claim 13, wherein the resilient part is formed to have an inner diameter which is less than a diameter of the head.

15. The artificial hip joint prosthesis according to claim 14, wherein an inner edge of each unit resilient portion is formed with a second inclined surface which has an inclination substantially corresponding to a surface curvature of the head to allow insertion and removal of the head into and out of the flexible joint member.

16. The artificial hip joint prosthesis according to claim 1, wherein the flexible joint member has an inner diameter which corresponds to the diameter of the head.

17. The artificial hip joint prosthesis according to claim 2, wherein a plurality of through-holes are defined through the middle part in a manner such that they are spaced apart one from another by a predetermined interval.

18. The artificial hip joint prosthesis according to claim 9, wherein the projecting ribs project radially inward adjacent to the entrance of and from the inner surface of the pelvis-contacting element and have the preselected depth, and the engaging grooves are defined on the outer surface of the resilient part and extend in the circumferential direction.

19. The artificial hip joint prosthesis according to claim 1, wherein the resilient part has a polygonal configuration.

20. An artificial hip joint prosthesis for installation between a pelvis and a femur to allow the femur to be rotated relative to the pelvis, comprising:

a pelvis-contacting element having a truncated hollow sphere-shaped configuration;

a stem capable of being fixed to the femur;

a head integrally coupled to a distal end of the stem and having a truncated sphere-shaped configuration; and a flexible joint member interposed between the pelvis-contacting element and the stem to accommodate and rotatably support the head, the flexible joint member comprising:

a body part having a configuration of a hollow hemisphere;

a resilient part formed at an entrance of the body part to have a predetermined thickness, the resilent part having (i) a substantially ring-shaped configuration, (ii) pair slits so that the resilient part is divided into a pair of unit resilient portions which are separated by a predetermined distance and symmetrical with each other, and (iii) a pair of flattened portions formed on an outer surface of the resilient part at regions corresponding to the slits each to extend through a predetermined angle in the circumferential direction; and a depressed part between the body part and the resilient part, the depressed part having a measurable thickness and a pair of through-holes defined in the depressed part such that they are opposite each other, wherein the depressed part is formed on an outer surface of the flexible joint member to have a predetermined depth and continuously extends along the circumferential directions, wherein the slits are defined in the resilient part at regions corresponding to the through-holes.

21. The artificial hip joint prosthesis according to claim 20, wherein a pair of decoupling grooves are defined on the outer surface of the resilient part to be aligned on a line which is orthogonal to another line connecting the slits and thereby spaced apart from the slits by 90 in the circumferential direction, so that the flexible joint member can be decoupled from the pelvis-contacting element by pressing radially inward the resilient part in the decoupling grooves.

22. The artificial hip joint prosthesis according to claim 21, wherein the pair of decoupling grooves serve as tool passage openings so that a tool can be placed between the pelvis-contacting element and the flexible joint member when the flexible joint member is coupled to the pelvis-contacting element.

23. The artificial hip joint prosthesis according to claim 20, wherein the resilient part is formed to have an outer diameter which is greater than a diameter of the entrance of the pelvis-contacting element.

24. The artificial hip joint prosthesis according to claim 23, wherein the resilient part is formed to have an inner diameter which is less than a diameter of the head.

25. The artificial hip joint prosthesis according to claim 24, wherein an inner edge of each unit resilient portion is formed with a second inclined surface which has an inclination substantially corresponding to a surface curvature of the head to allow insertion and removal of the head into and out of the flexible joint member.

26. An artificial hip joint prosthesis for installation between a pelvis and a femur to allow the femur to be rotated relative to the pelvis, comprising:

a pelvis-contacting element having a truncated hollow sphere-shaped configuration;
a stem capable of being fixed to the femur;
a head integrally coupled to a distal end of the stem and having a truncated sphere-shaped configuration; and
a flexible joint member interposed between the pelvis-contacting element and the stem to accommodate and rotatably support the head, the flexible joint member comprising:
a body part having a configuration of a hollow hemisphere;
a substantially ring shaped resilient part formed at an entrance of the body part to have a predetermined thickness, the resilient part having at least one slit to allow expansion of the resilient part; and
a middle part between the body part and the resilient part, the middle part having at least one through-hole that is wider than the slit in the resilient part,
wherein projecting ribs are formed on an outer surface of the resilient part to project radially outward from the outer surface of the resilient part and extend in the circumferential direction, and engaging grooves corresponding to the projecting ribs are defined on the inner surface of the pelvis-contacting element to have a preselected depth and placed adjacent to an entrance of the pelvis-contacting element, and
wherein each projecting rib has a first inclined surface which is inclined downward by a preselected angle when measured in a direction where the flexible joint member is inserted into the pelvis-contacting element.

* * * * *